US012766047B2

(12) United States Patent
Moore

(10) Patent No.: US 12,766,047 B2
(45) Date of Patent: Oct. 20, 2026

(54) FEMININE PANTS PROTECTOR

(71) Applicant: Sandra Faye Moore, Asheville, NC (US)

(72) Inventor: Sandra Faye Moore, Asheville, NC (US)

( * ) Notice: Subject to any disclaimer, the term of this patent is extended or adjusted under 35 U.S.C. 154(b) by 267 days.

(21) Appl. No.: 18/629,045

(22) Filed: Apr. 8, 2024

(65) Prior Publication Data

US 2025/0312200 A1 Oct. 9, 2025

(51) Int. Cl.

| | |
|---|---|
| ***A61F 13/472*** | (2006.01) |
| ***A61F 13/15*** | (2006.01) |
| ***A61F 13/47*** | (2006.01) |
| ***A61F 13/56*** | (2006.01) |

(52) U.S. Cl.

CPC ........ *A61F 13/472* (2013.01); *A61F 13/5611* (2013.01); *A61F 13/5616* (2013.01); *A61F 2013/15373* (2013.01); *A61F 2013/4708* (2013.01)

(58) Field of Classification Search

CPC .......................... A61F 13/472; A61F 13/5611; A61F 13/5616; A61F 2013/15373; A61F 2013/4708; A61F 13/66; A61F 13/82; A61F 13/47218; A61F 2013/4706; A61F 13/47236; A41D 31/10; A41D 27/13; A41B 9/12; A41B 9/002; B60N 2/665; Y10T 428/1471

See application file for complete search history.

(56) References Cited

U.S. PATENT DOCUMENTS

| | | | | | |
|---|---|---|---|---|---|
| 1,897,952 | A * | 2/1933 | Dupont | A41D 27/13 | 2/58 |
| 2,476,112 | A * | 7/1949 | Pinchoff | A41D 27/12 | 2/231 |
| 4,605,404 | A * | 8/1986 | Sneider | A61B 10/0012 | 604/389 |
| 5,978,970 | A * | 11/1999 | Bright | B62J 1/007 | 2/467 |
| 6,680,421 | B1 * | 1/2004 | Ravo | A61F 13/4758 | 604/358 |
| 7,512,995 | B2 * | 4/2009 | Deffner | A41D 1/086 | 2/227 |
| 8,042,194 | B2 * | 10/2011 | Connor | A61F 13/47236 | 604/389 |

(Continued)

FOREIGN PATENT DOCUMENTS

| | | | |
|---|---|---|---|
| CN | 200991359 | * 12/2007 | A61F 13/15 |

*Primary Examiner* — Michele Kidwell

(74) *Attorney, Agent, or Firm* — Coffield Heedy Kilgore PLLC; William G. Heedy

(57) ABSTRACT

A feminine pants protector for use in combination with a pair of pants includes a top side and a bottom side; an absorbent segment; a first wing segment and a second wing segment each extending from the absorbent segment; a plurality of adhesive strips on the bottom side, each one of the plurality of adhesive strips being structured and disposed for selectively adhering the bottom side to the inner facing crotch surface and inner facing leg surfaces of the pair of pants such that the absorbent segment is positioned against the inner facing crotch surface and each of the first and second wing segments is against a respective one of the inner facing leg surfaces; and wherein the absorbent segment is positioned to absorb bodily fluids when the pants are worn.

8 Claims, 4 Drawing Sheets

(56) References Cited

U.S. PATENT DOCUMENTS

| | | | | |
|---|---|---|---|---|
| 8,591,488 | B2 * | 11/2013 | Brezoczky | A61F 13/82 604/385.03 |
| 2004/0068247 | A1 * | 4/2004 | Connor | A61F 13/5611 604/387 |
| 2004/0186448 | A1 * | 9/2004 | Misek | A61F 13/15203 604/385.01 |
| 2007/0135788 | A1 * | 6/2007 | Damay | A61F 13/4704 604/385.01 |
| 2010/0152693 | A1 * | 6/2010 | Lira | A61F 13/47227 604/378 |
| 2016/0278991 | A1 * | 9/2016 | Lumaque-Steeman | A61F 13/471 |

* cited by examiner

FEMININE PANTS PROTECTOR

FIELD OF INVENTION

This invention relates to feminine hygiene and, more particularly, a single-use pad that may be releasably adhered to the inner facing surface of a feminine pair of pants for protecting the pants from being soiled.

BACKGROUND

Traditional feminine hygiene products often fall short in providing adequate coverage for leaks and stains, particularly for women who choose not to wear underwear or experience urinary incontinence due to factors such as aging or childbirth. Additionally, uncertainties surrounding menstrual cycles can lead to unexpected leaks and stains, causing embarrassment and inconvenience.

Previous attempts to address the need for discreet and reliable protection against bodily fluids in women have often fallen short due to various limitations. Traditional feminine hygiene products such as pads and liners, while effective to some extent, may lack the absorbency or coverage needed to handle the diverse range of fluids women encounter throughout the day and night. Additionally, these products may not provide adequate breathability, leading to discomfort and potential skin irritation. Disposable underwear options exist, but they can be bulky, costly, and environmentally unfriendly. Similarly, some reusable options may lack the necessary absorbency or may not be designed to fit comfortably under clothing. Other solutions such as waterproof underwear or protective clothing may offer protection but compromise on comfort and discretion. Overall, these attempts have failed to offer a comprehensive solution that meets the diverse needs of women seeking discreet and reliable protection against urinary incontinence, menstrual leaks, and other bodily fluids, while also considering factors such as comfort, affordability, and sustainability.

In view of the problems discussed above, there exists a need for a low-cost, single-use pad that may be releasably adhered to the inner facing surface of a feminine pair of pants for protecting the pants from being soiled.

DETAILED DESCRIPTION

As discussed herein, a feminine pants protector 10 is provided for use in combination with a pair of pants 100 for absorbing—and therefore concealing—bodily fluids, such as those resulting from urinary incontinence, menstrual leaks, and other bodily fluids.

Figure 1:
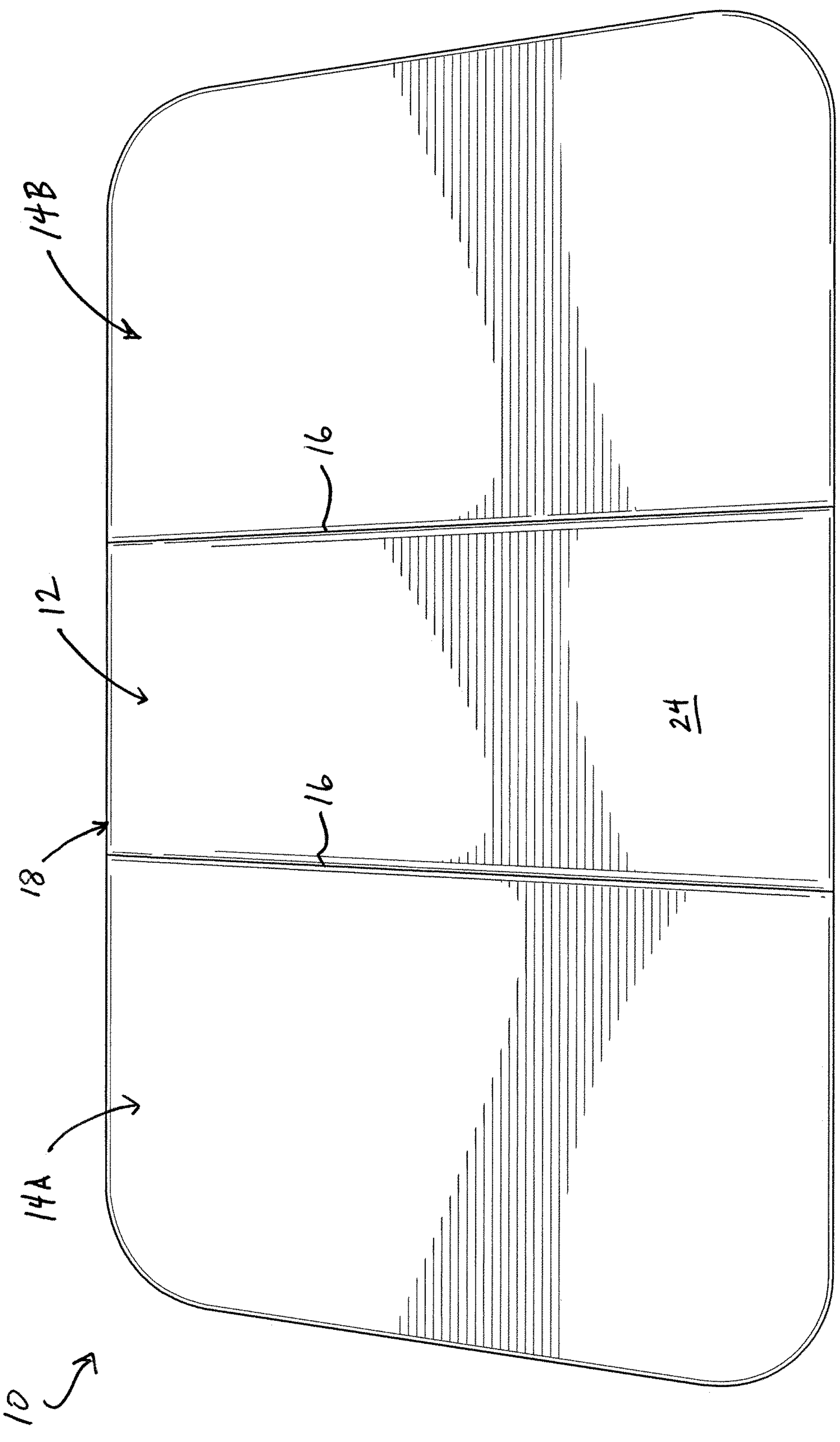
FIG. 1 is a perspective view of the top side of a feminine pants protector.

FIG. 1 is a perspective view of the top side 18 of the feminine pants protector 10 showing three segments, including an absorbent segment 12 and wing segments 14A and 14B on opposing ends of the absorbent segment 12. The absorbent segment 12 and opposing wings segments 14A and 14B may be connected at a pre-fabricated fold line 16 such that the wing segments 14A and 14B may be easily folded relative to the absorbent segment 12 with limited stretching or other distortion of the absorbent segment 12.

Figure 2:
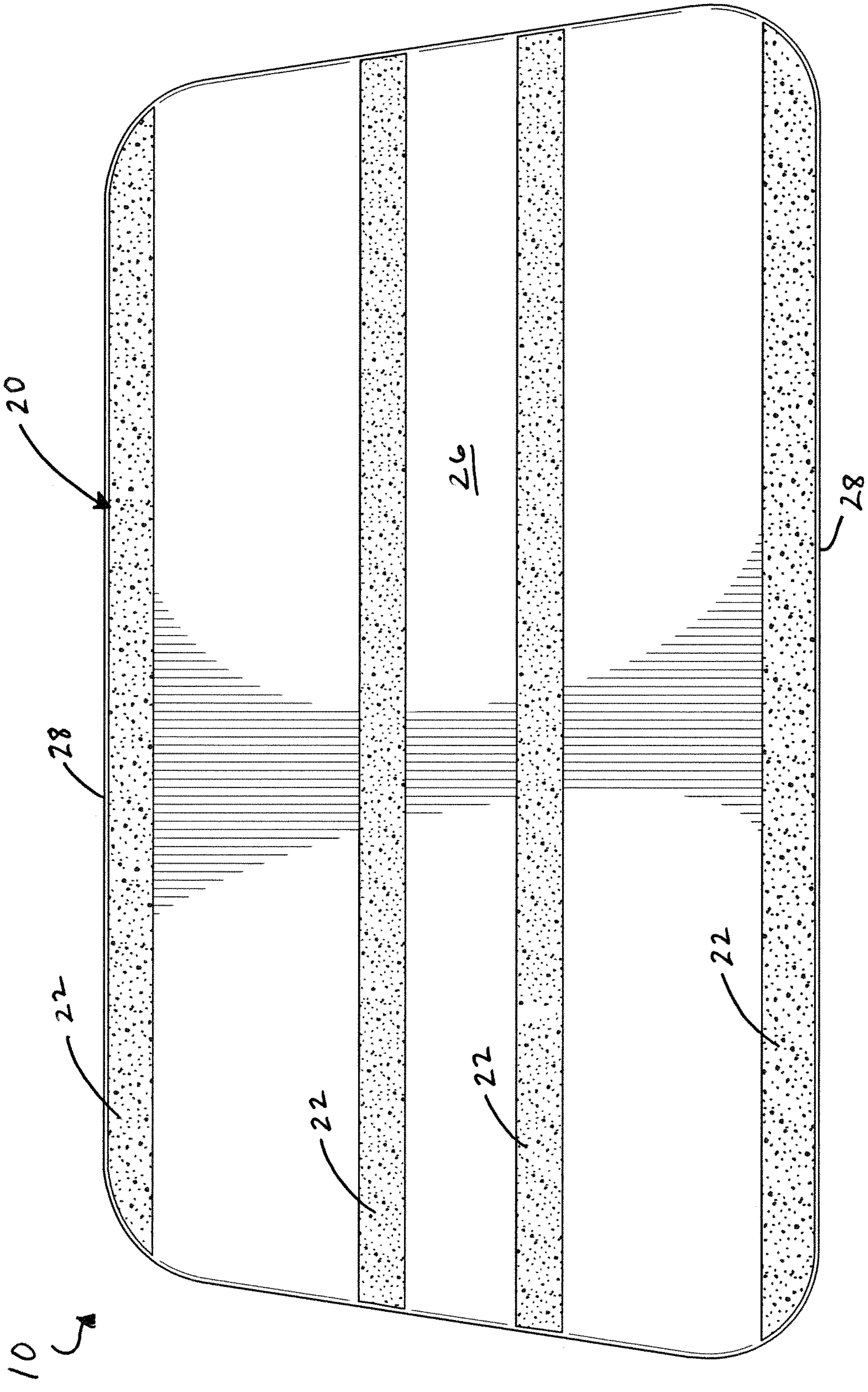
FIG. 2 is a perspective view of the bottom side thereof.

FIG. 2 is a perspective view of the bottom side 20 of the feminine pants protector 10 showing a plurality of adhesive strips 22 on the bottom side 20 of the feminine pants protector 10. Each one of the plurality of adhesive strips 22 is structured and disposed for selectively adhering the feminine pants protector 10 to clothing and other various materials.

In an embodiment, the absorbent segment 12 is one-eighth (⅛) inches thick, defining a first thickness 23, and is formed from a highly absorbent material 24, such as a thick sanitary napkin material.

In an embodiment, each of the wing segments 14 is one-sixteenth (1/16) inches thick, defining a second thickness 25, and is formed from any suitable material, such as a thin sanitary napkin material.

In an embodiment, the bottom side 20 includes a fluid barrier layer 26 for confining the bodily fluids within the absorbent segment 12.

In an embodiment, the feminine pants protector 10 measures 6.75" wide by 9.5" long, with the absorbent segment 12 measuring 2.5" long and each wing segment 14 measuring 3.5" long, which are sizes selected for fitting within most pants. Other sizes suitable for fitting pants may also be used.

In an embodiment, the plurality of adhesive strips 22 includes four adhesive strips 22.

In an embodiment, each one of the plurality of adhesive strips 22 runs the entire length of the feminine pants protector 10.

In an embodiment, first and second adhesive strips run the length of the perimeter ends 28 of the bottom side 20.

Figure 3:
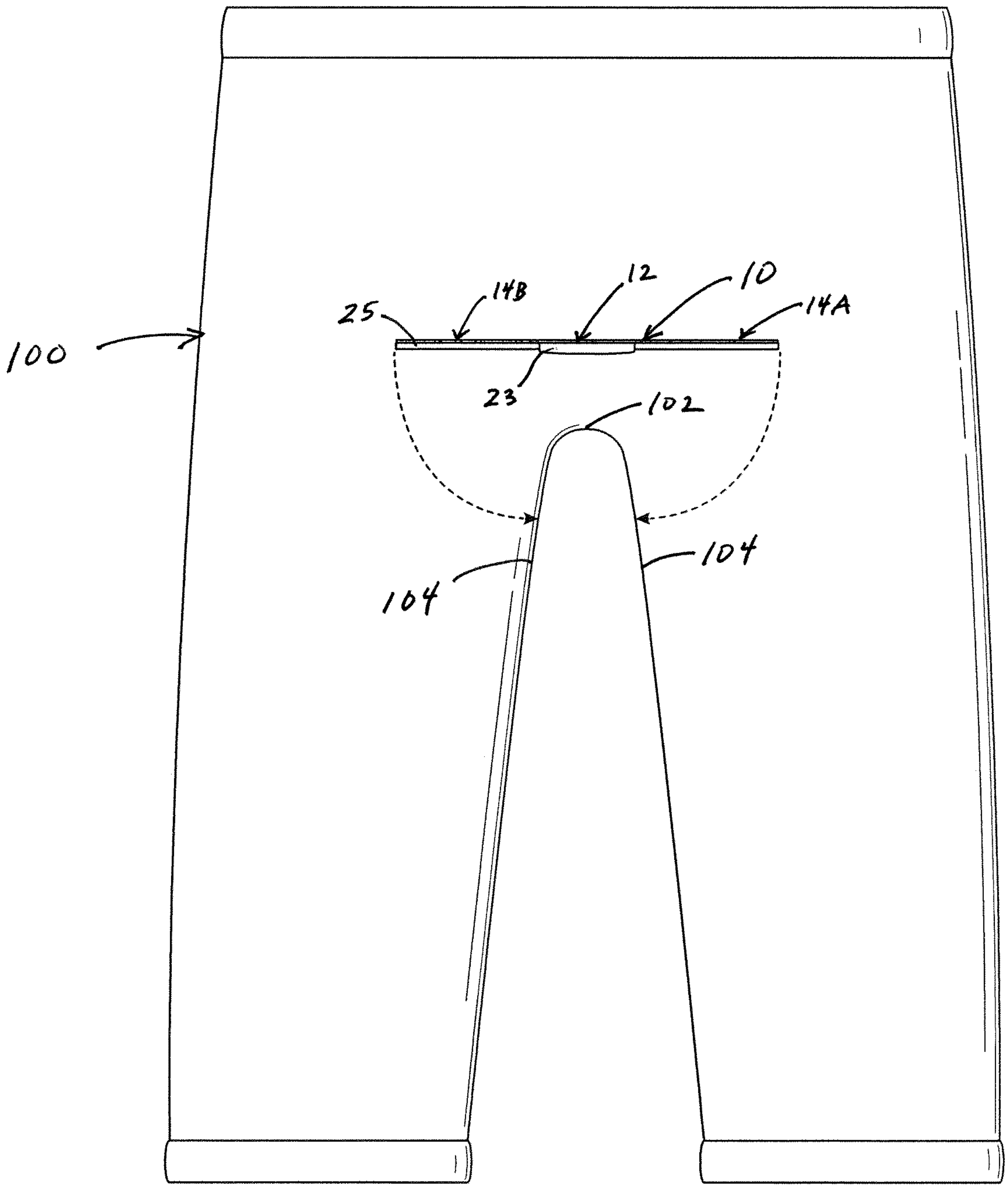
FIG. 3 is a front elevation view showing the feminine pants protector being applied to the inner facing surfaces of a pair of pants.
Figure 4:
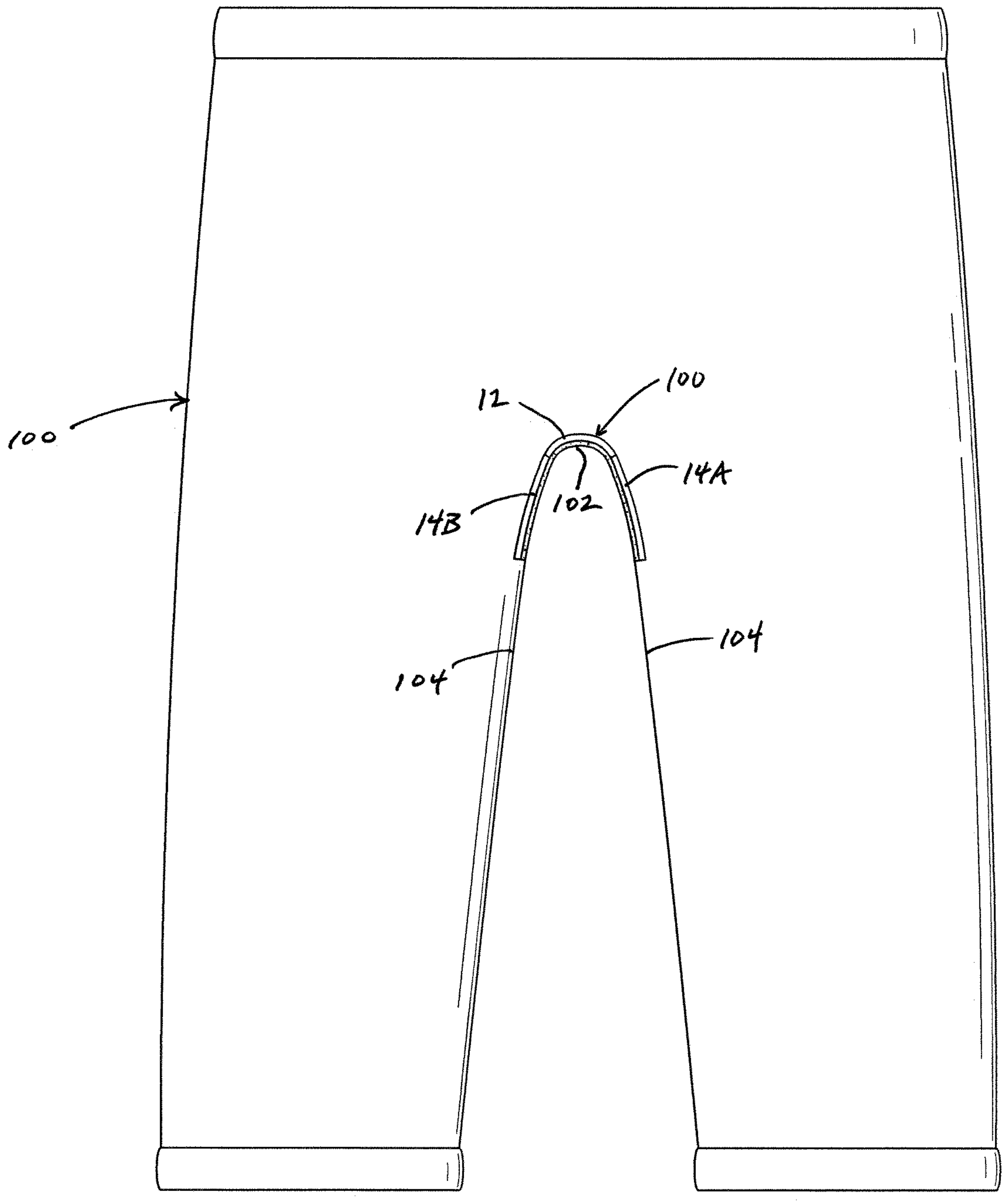
FIG. 4 is a front elevation view showing the feminine pants protector applied to the inner facing surfaces of a pair of pants.

With reference to FIGS. 3-4, the feminine pants protector 10 is adhered to the pants 100 by applying the plurality of adhesive strips 22 on the bottom side 20 of the feminine pants protector 10 to the inner facing crotch surface 102 and inner facing leg surfaces 104 such that the absorbent segment 12 is centrally positioned against the inner facing crotch surface 102.

In operation, the feminine pants protector 10 provides discreet protection for women against various bodily fluids, including urine, menstrual blood, fluids of a sexual nature and any other fluids, wherein the absorbent segment 12 absorbs the fluid. Once soiled, the wearer may remove the feminine pants protector 10 from the pants 100 and dispose of the feminine pants protector 10.

As described herein, a feminine pants protector 10 for use in combination with a pair of pants 100 having an inner facing crotch surface 102 and inner facing leg surfaces 104 includes:

- a top side 18 and a bottom side 20;
- an absorbent segment 12 having a first thickness 23;
- a first wing segment 14A and a second wing segment 14B each extending from the absorbent segment 12, each of the first and second wing segments 14A and 14B having a second thickness 25;
- the first thickness 23 being greater than the second thickness 25;
- a plurality of adhesive strips 22 on the bottom side 20, each one of the plurality of adhesive strips 22 being structured and disposed for selectively adhering the bottom side 20 to the inner facing crotch surface 102 and inner facing leg surfaces 104 of the pair of pants 100 such that the absorbent segment 12 is positioned against the inner facing crotch surface 102 and each of the first and second wing segments 14A and 14B is against a respective one of the inner facing leg surfaces 104; and wherein the absorbent segment 12 is positioned to absorb bodily fluids when the pants 100 are worn.

The figures and descriptions provided herein may have been simplified to illustrate aspects that are relevant for a clear understanding of the herein described devices, systems, and methods, while eliminating, for the purpose of clarity, other aspects that may be found in typical devices, systems, and methods. Those of ordinary skill may recognize that other elements and/or operations may be desirable and/or necessary to implement the devices, systems, and methods described herein. Because such elements and operations may be well known in the art, and because they do not facilitate a better understanding of the present disclosure, a discussion of such elements and operations is not provided herein. The present disclosure is deemed to inherently include all such elements, variations, and modifications to the described aspects that would be known to those of ordinary skill in the art, particularly in view of reading the present disclosure. Any headings used herein are for organizational purposes only and are not meant to be used to limit the scope of the description or the claims.

The terminology used herein is for the purpose of describing particular example embodiments or implementations only and is not intended to be limiting. As used herein, the singular forms “a”, “an”, and “the” may be intended to include the plural forms as well, unless the context clearly indicates otherwise.

The terms “comprises,” “comprising,” “includes,” “including,” “has,” “having,” and variations in form thereof are inclusive or variations in form thereof are intended to be inclusive in a manner similar to the term “comprises” as that term is interpreted when employed as a transitional word in a claim, and therefore specify the presence of stated features, integers, steps, operations, elements, and/or components, but do not preclude the presence or addition of one or more other features, integers, steps, operations, elements, components, and/or groups thereof unless explicitly stated otherwise or the context clearly requires otherwise.

The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being “on”, “engaged to”, “connected to” or “coupled to” another element or layer, it may be directly on, engaged, connected or coupled to the other element or layer, or intervening elements or layers may be present. In contrast, when an element is referred to as being “directly on,” “directly engaged to”, “directly connected to” or “directly coupled to” another element or layer, there may be no intervening elements or layers present. Other words used to describe the relationship between elements should be interpreted in a like fashion (e.g., “between” versus “directly between,” “adjacent” versus “directly adjacent,” etc.). As used herein, the term “and/or” includes any and all combinations of one or more of the associated listed items.

Although the terms first, second, third, etc., may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as “first,” “second,” and other numerical terms when used herein do not imply a sequence or order unless clearly indicated by the context. Thus, a first element, component, region, layer or section discussed below could be termed a second element, component, region, layer or section without departing from the teachings of the exemplary embodiments and implementations.

Unless otherwise defined, all terms (including technical and scientific terms) used herein have the same meaning as commonly understood by one of ordinary skill in the art to which this subject matter belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. For brevity and/or clarity, well-known functions or constructions may not be described in detail herein.

The terms “for example” and “such as” mean “by way of example and not of limitation.” The subject matter described herein is provided by way of illustration for the purposes of teaching, suggesting, and describing, and not limiting or restricting. Combinations and alternatives to the illustrated embodiments and implementations are contemplated, described herein, and set forth in the claims.

The term “exemplary” is used herein to mean serving as an example, instance, or illustration. Any aspect or design described herein as “exemplary” is not necessarily to be construed as preferred or advantageous over other aspects or designs. Similarly, examples are provided herein solely for purposes of clarity and understanding and are not meant to limit the subject innovation or portion thereof in any manner.

For convenience of discussion herein, when there is more than one of a component, that component may be referred to herein either collectively or singularly by the singular reference numeral unless expressly stated otherwise or the context clearly indicates otherwise. For example, components N (plural) or component N (singular) may be used unless a specific component is intended. Also, the singular forms “a,” “an,” and “the” are intended to include the plural forms as well, unless expressly stated otherwise or the context indicates otherwise.

The terms “includes,” “has,” “having,” or “exhibits,” or variations in form thereof are intended to be inclusive in a manner similar to the term “comprises” as that term is interpreted when employed as a transitional word in a claim.

It will be understood that when a component is referred to as being “connected” or “coupled” to another component, it can be directly connected or coupled or coupled by one or more intervening components unless expressly stated otherwise or the context clearly indicates otherwise.

The term “and/or” includes any and all combinations of one or more of the associated listed items.

As used herein, phrases such as “between X and Y” and “between about X and Y” should be interpreted to include X and Y unless expressly stated otherwise or the context clearly indicates otherwise.

Terms such as “about”, “approximately”, “around”, and “substantially” are relative terms and indicate that, although two values may not be identical, their difference is such that the apparatus or method still provides the indicated or desired result, or that the operation of a device or method is not adversely affected to the point where it cannot perform its intended purpose. As an example, and not as a limitation, if a height of “approximately X inches” is recited, a lower or higher height is still "approximately X inches" if the desired function can still be performed or the desired result can still be achieved.

While terms such as vertical, horizontal, upper, lower, bottom, top, and the like may be used herein, it is to be understood that these terms are used for case in referencing the drawing and, unless otherwise indicated or required by context, does not denote a required orientation.

The different advantages and benefits disclosed and/or provided by the implementation(s) disclosed herein may be used individually or in combination with one, some or possibly even all of the other benefits. Furthermore, not every implementation, nor every component of an implementation, is necessarily required to obtain, or necessarily required to provide, one or more of the advantages and benefits of the implementation.

Conditional language, such as, among others, "can", "could", "might", or "may", unless specifically stated otherwise, or otherwise understood within the context as used, is generally intended to convey that certain embodiments and implementations preferably or optionally include certain features, elements and/or steps, while some other embodiments and implementations optionally do not include those certain features, elements and/or steps. Thus, such conditional language indicates, in general, that those features, elements and/or steps are used in a permissive sense rather than a mandatory sense, and may not be required for every implementation or embodiment.

The subject matter described herein is provided by way of illustration only and should not be construed as limiting the nature and scope of the claims herein. While different embodiments and implementations have been provided above, it is not possible to describe every conceivable combination of components or methodologies for implementing the disclosed subject matter, and one of ordinary skill in the art may recognize that further combinations and permutations that are possible. Furthermore, the nature and scope of the claims is not necessarily limited to implementations that solve any or all disadvantages which may have been noted in any part of this disclosure. Various modifications and changes may be made to the subject matter described herein without departing from the spirit and scope of, the exemplary embodiments, implementations, and applications illustrated and described herein.

Although the subject matter presented herein has been described in language specific to components used therein, it is to be understood that the scope of the claims is not necessarily limited to the specific components or characteristics thereof described herein; rather, the specific components and characteristics thereof are disclosed as example forms of implementing the disclosed subject matter. Accordingly, the disclosed subject matter is intended to embrace all alterations, modifications, and variations, that fall within the scope and spirit of any claims included herein or that may be written.

The foregoing description and figures are intended only to convey to a person having ordinary skill in the art the fundamental aspects of the disclosed subject matter and are not intended to limit, and should not be construed as limiting, the scope of any present or future claims. Further, in the foregoing Detailed Description, various features may be grouped together in a single embodiment or implementation for the purpose of streamlining the disclosure. This method of disclosure is not to be interpreted as reflecting an intention that a claimed embodiment, implementation, or application requires more features than are expressly recited in a present or future claim. Rather, present and future claims reflect patentable subject matter which may lie in less than all features of a single disclosed embodiment, implementation, or application.

The invention claimed is:

1. A feminine pants protector for use in combination with a pair of pants having an inner facing crotch surface and inner facing leg surfaces, the feminine pants protector comprising:

a top side and a bottom side;

an absorbent segment having a first thickness, the absorbent segment being formed from a highly absorbent material;

a first wing segment and a second wing segment each extending from the absorbent segment, each of the first and second wing segments having a second thickness;

a pre-fabricated fold line defined between the absorbent segment and each of the first and second wing segments, the first and second wing segments being foldable relative to the absorbent segment about the respective fold lines;

the first thickness being greater than the second thickness;

a plurality of adhesive strips on the bottom side, the plurality of adhesive strips comprising four adhesive strips, each one of the plurality of adhesive strips extending continuously along an entire length of the feminine pants protector across the first wing segment, the absorbent segment, and the second wing segment and across the respective fold lines, the four adhesive strips including first and second adhesive strips running the length of opposing perimeter ends of the bottom side, each one of the plurality of adhesive strips being structured and disposed for selectively adhering the bottom side to the inner facing crotch surface and inner facing leg surfaces of the pair of pants such that the absorbent segment is positioned against the inner facing crotch surface and each of the first and second wing segments is against a respective one of the inner facing leg surfaces;

the bottom side including a fluid barrier layer confining bodily fluids within the absorbent segment; and wherein the absorbent segment is positioned to absorb bodily fluids when the pants are worn.

2. The feminine pants protector as recited in claim 1 wherein the first thickness is twice the second thickness.

3. The feminine pants protector as recited in claim 1 wherein first thickness is one-eighth (⅛) inches.

4. The feminine pants protector as recited in claim 1 wherein second thickness is one-sixteenth (1/16) inches.

5. The feminine pants protector as recited in claim 1 wherein the highly absorbent material is a thick sanitary napkin material.

6. The feminine pants protector as recited in claim 1 wherein the bottom side includes a fluid barrier layer.

7. The feminine pants protector as recited in claim 1 wherein the absorbent segment measures 2.5 inches long and each wing segment measures 3.5 inches long.

8. The feminine pants protector as recited in claim 1 wherein the absorbent segment and each wing segment measures 6.75 inches wide.

* * * * *